US011672789B2

(12) United States Patent
Brown et al.

(10) Patent No.: US 11,672,789 B2
(45) Date of Patent: Jun. 13, 2023

(54) RADIATION MITIGATOR AND METHOD OF USE THEREOF

(71) Applicants: Georgetown University, Washington, DC (US); The Board of Regents of the University of Oklahoma, Norman, OK (US)

(72) Inventors: Milton L. Brown, Brookeville, MD (US); Yali Kong, Fairfax, VA (US); Courtney Houchen, Edmond, OK (US); Sripathi M. Sureban, Oklahoma City, OK (US); Parthasarathy Chandrakesan, Edmond, OK (US)

(73) Assignees: Georgetown University, Washington, DC (US); The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 17/728,485

(22) Filed: Apr. 25, 2022

(65) Prior Publication Data

US 2023/0033749 A1 Feb. 2, 2023

Related U.S. Application Data

(63) Continuation of application No. 16/089,794, filed as application No. PCT/US2017/025440 on Mar. 31, 2017, now Pat. No. 11,311,526.

(60) Provisional application No. 62/316,121, filed on Mar. 31, 2016.

(51) Int. Cl.
 *A61K 31/454* (2006.01)
 *A61P 39/00* (2006.01)
 *A61K 31/4184* (2006.01)

(52) U.S. Cl.
 CPC ........ *A61K 31/454* (2013.01); *A61K 31/4184* (2013.01); *A61P 39/00* (2018.01)

(58) Field of Classification Search
 CPC .... A61K 31/454; A61K 31/4184; A61P 39/00
 See application file for complete search history.

(56) References Cited

U.S. PATENT DOCUMENTS

| | | |
|---|---|---|
| 9,233,943 B2 | 1/2016 | Gadakh et al. |
| 9,233,949 B2 | 1/2016 | Brown et al. |
| 11,311,526 B2 | 4/2022 | Brown et al. |
| 2011/0135641 A1 | 6/2011 | Isenberg et al. |
| 2012/0196896 A1 | 8/2012 | Brown et al. |
| 2020/0306234 A1 | 10/2020 | Brown et al. |

FOREIGN PATENT DOCUMENTS

WO  WO-2015/120458 A1  8/2015

OTHER PUBLICATIONS

Ambade et al., "Oxidative Stress and Inflammation: Essential Partners in Alcoholic Liver Disease," International Journal of Hepatology, vol. 2012, Article ID 853175, 9 pages (2012).
Bitanihirwe et al., "Oxidative Stress in Schizophrenia: An Integrated Approach," Neurosci Biobehav Rev., 35(3): 878-893 (2011).
Charrier et al., "Inhibition of Angiotensin I-converting Enzyme Induces Radioprotection by Preserving Murine Hematopoietic Short-term Reconstituting Cells," Blood, 104:978-985 (2004).
Cohen et al., "Radiation Nephropathy is not Mitigated by Antagonists of Oxidative Stress," Radiation Research, 172: 260-264 (2009).
Dantas et al., "Oxidative Stress Responses in the Human Fungal Pathogen, *Candida albicans*," Biomolecules, 5: 142-165 (2015).
Dogru et al., "Potential Role of Oxidative Stress in Ocular Surface Inflammation and Dry Eye Disease," Invest Ophthalmol Vis Sci., 59: DES163-DES168 (2018).
International Preliminary Report on Patentability for International Application No. PCT/US2017/025440 dated Oct. 2, 2018.
International Search Report and Written Opinion for International Application No. PCT/US17/25440 dated Sep. 11, 2017.
Kruk et al., "Oxidative Stress and Skin Diseases: Possible Role of Physical Activity," Asian Pac J Cancer Prev, 15(2): 561-568 (2014).
Kumar et al., "Oxidative Stress in Oral Diseases: Understanding Its Relation with Other Systemic Diseases," Front. Physiol., 8:693 (2017).
Liou et al., "Reactive oxygen species in cancer," Free Radic Res., 44(5): 479-496 (2010).
Misra et al., "Oxidative stress and ischemic myocardial syndromes." Med Sci Monit, 15(10): RA209-219 (2009).

(Continued)

*Primary Examiner* — Kamal A Saeed
(74) *Attorney, Agent, or Firm* — Foley Hoag LLP; Dana M. Gordon

(57) ABSTRACT

Provided are methods useful for preventing and mitigating radiation injury, including acute radiation syndrome, comprising administering to a subject a therapeutically effective amount of a compound represented by formula I

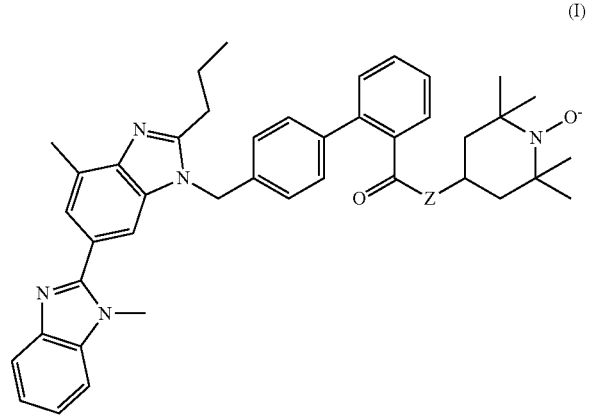

or a pharmaceutically acceptable salt thereof, wherein Z is —O— or —N(H)—.

18 Claims, 12 Drawing Sheets

(56) References Cited

OTHER PUBLICATIONS

Rahman et al., "Oxidative stress and redox regulation of lung inflammation in COPD," Eur Respir J, 28:219-242 (2006).
Robbins et al., Chronic oxidative stress and radiation-induced late normal tissue injury: a review, Int J Radiat Biol, 80(4): 251-259 (2004).
Su et al., "Oxidative Stress Signaling in Alzheimer's Disease," Curr Alzheimer Res., 5(6): 525-532 (2008).
Valyi-Nagy et al., "Role of oxidative damage in the pathogenesis of viral infections of thenervous system," Histol Histopathol 20: 957-967 Abstract Only (2005).
Zhang et al., "Flaviviridae Viruses and Oxidative Stress: Implications for Viral Pathogenesis," Oxidative Medicine and Cellular Longevity, vol. 2019, Article ID 1409582, 17 pages (2019).

* = compared to vehicle control. * = p<0.0001;  = p<0.001; * = p<0.01

* = compared to vehicle control. ** = p<0.00001; * = p<0.0001; ** = p<0.001; * = p<0.01
# = compared to Basal (No IR). # = p<0.001

* = compared to vehicle control. * = p<0.0001;  = p<0.001; * = p<0.01

* = compared to vehicle control. * = p<0.0001;  = p<0.001; * = p<0.01

\* = compared to vehicle control. \*\*\*\* = p<0.00001; \*\*\* = p<0.0001; \*\* = p<0.001; \* = p<0.01
# = compared to Basal (No IR). # = p<0.001

RADIATION MITIGATOR AND METHOD OF USE THEREOF

CROSS REFERENCE TO RELATED APPLICATIONS

This application claims benefit of priority to U.S. Provisional Application No. 62/316,121, filed Mar. 31, 2016.

BACKGROUND

Ionizing radiation, i.e., radiation with energy high enough to have the potential of ionizing molecules in a living body, may cause serious damage and injury to the cells and tissues of living beings. Ionizing radiation damages tissue by direct ionization, which disrupts molecules directly, and also by producing highly reactive free radicals, which attack nearby cells. The net effect is that biological molecules suffer local disruption; this may exceed the body's capacity to repair the damage and may cause mutations in cells currently undergoing replication that lead to diseases. In consequence, dysfunction of many important organs, and even multiple organ failure, can occur, which in turn can eventually lead to death (radiation-induced lethality).

Damaging and harmful effects of radiation can be observed both in the case of acute high dose exposure and in the case of chronic exposure to lower doses. These effects include so-called radiation sickness caused by chronic exposure to the radiation emitting environment, and acute radiation syndrome (poisoning), caused by acute exposure to the internal or external action of a radioactive material or a source of radiation.

Chronic exposure to low doses of radiation, particularly ionizing radiation such as gamma rays, has mutagenic activity and brings a risk of developing cancer. Harmful effects of the radiation can be also due to the exposure of a patient or medical staff to the radiation during routine radiodiagnostic procedures or radiotherapy, e.g., radiotherapy of a cancer, where radiation which destroys cancer cells can at the same time damage healthy, normal cells. This is one of the main off-target effects of radiotherapy of a cancer, which is urgently needed to be fixed by developing effective mitigators.

Injuries to the bone marrow and gastrointestinal (GI) tract are the main determinants of lethality after total-body irradiation (TBI). Natural and therapeutic protection against radiation-induced injury is mediated by various mechanisms such as free-radical scavenging, calcium channel blockade, inhibition of lipid peroxidation, enhancement of DNA damage response (DDR) for effective DNA damage repair, and stimulation of stem cell and or stem-like cell activity.

Radioprotectors are compounds like anti-oxidants that can reduce the damage in normal tissues caused by radiation only if applied before or at the time of radiation. Among them are aminothiol compounds, like mercaptamine, glutathione, amifostine, and their phosphorylated pro-drugs. Aminothiol protectants exert their effect through their free-radical scavenging and antioxidant ability, and they must be given prior to radiation exposure to provide effective protection. A disadvantage and the main limitation of aminothiol-based radioprotectors is their high toxicity, especially at concentrations required for radioprotection, low efficiency when used after the radiation exposure, lack of protection against radiation-induced lethality/mortality, and generally low degree of protection.

In contrast, mitigators may be used to minimize toxicity even after radiation has been delivered. In recent years there has been growing interest in biological treatments which could be administered after radiation exposure. This includes the use of agents, e.g., anti-apoptotic proteins, cell growth factors, G-CSF, and GM-CSF (filgrastim), which could increase survival after accidental radiation injuries. These drugs stimulate the growth of white blood cells and can help repair bone marrow damage. They also can be used in patients receiving radiation therapy.

Due to extensive use and presence of ionizing radiation and/or radiation sources in many fields of human activity, such as medicine, nuclear power plants, industry, as well as the threat of contamination caused by nuclear/terrorist attacks, the need still exists for radioprotectors and mitigators based on simple chemical molecules, which could be effective especially in reducing radiation-induced morbidity and mortality while being non-toxic and safe at concentrations required for effective protection.

SUMMARY

Provided are methods useful for preventing and mitigating radiation injury, including acute radiation syndrome. Certain embodiments of the present disclosure are used in preventing and mitigating radiation syndrome, including gastrointestinal (GI) acute radiation syndrome, and promoting overall survival following radiation injury in various settings, including without limitation nuclear disaster, accidental radiation exposure, acute radiation sickness, aviation, spaceflight and space travel, and protection and treatment of military personnel.

The present disclosure includes, for example, a method for treating or preventing radiation-induced tissue injury, comprising administering to a subject in need thereof a therapeutically effective amount of a compound represented by formula I

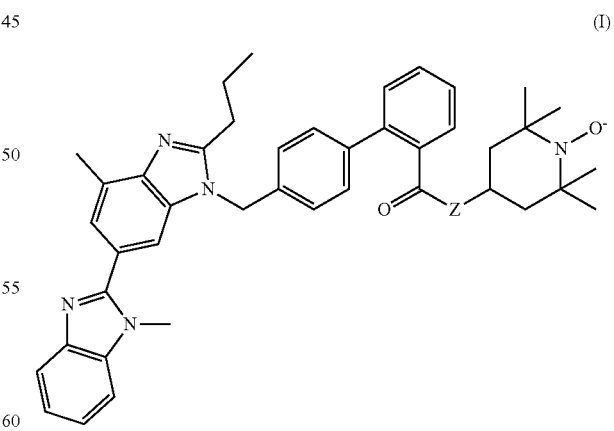

(I)

or a pharmaceutically acceptable salt thereof, wherein Z is —O— or —N(H)—, thereby treating or preventing radiation-induced tissue injury in the subject.

In certain embodiments, Z is —O— and the compound represented by formula I is (YK-4-250)

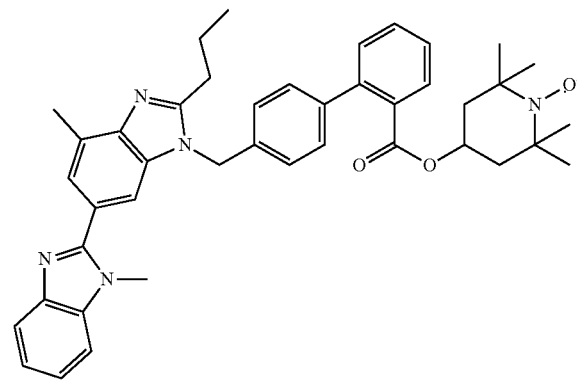

In certain embodiments, Z is —N(H)—.

The present disclosure further includes, for example, a method for treating or preventing radiation-induced tissue injury, comprising administering to a subject in need thereof a therapeutically effective amount of a compound represented by formula II (II)

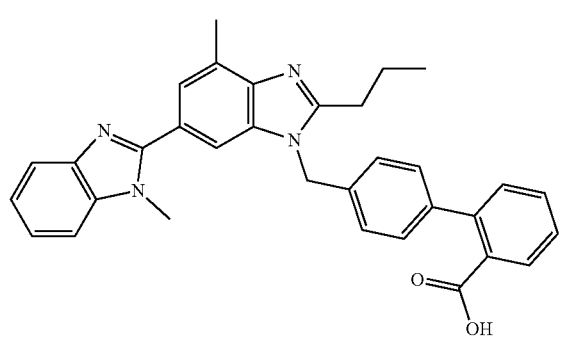

or a pharmaceutically acceptable salt thereof, thereby treating or preventing radiation-induced tissue injury in the subject.

The present disclosure further includes, for example, a method for treating or preventing radiation-induced tissue injury, comprising administering to a subject in need thereof a therapeutically effective amount of a compound represented by formula III (III)

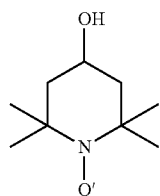

or a pharmaceutically acceptable salt thereof, thereby treating or preventing radiation-induced tissue injury in the subject.

The present disclosure further includes, for example, a method for treating or preventing radiation-induced tissue injury, comprising co-administering to a subject in need thereof a therapeutically effective amount of a compound represented by formula II (II)

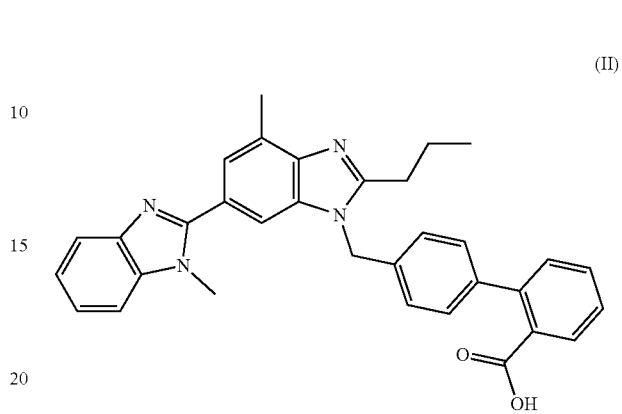

or a pharmaceutically acceptable salt thereof, and a therapeutically effective amount of a compound represented by formula III (III)

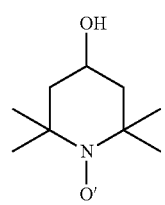

or a pharmaceutically acceptable salt thereof, thereby treating or preventing radiation-induced tissue injury in the subject.

Accordingly, in certain embodiments of the methods disclosed herein, the subject is a mammal.

Accordingly, in certain embodiments of the methods disclosed herein, the subject is a human.

Accordingly, in certain embodiments of the methods disclosed herein, the radiation-induced tissue injury is prevented.

Accordingly, in certain embodiments of the methods disclosed herein, the radiation-induced tissue injury is treated.

It will be understood that the preceding summary is not to be construed as limiting the inventive concepts described in the present disclosure.

DETAILED DESCRIPTION

Figure 1:
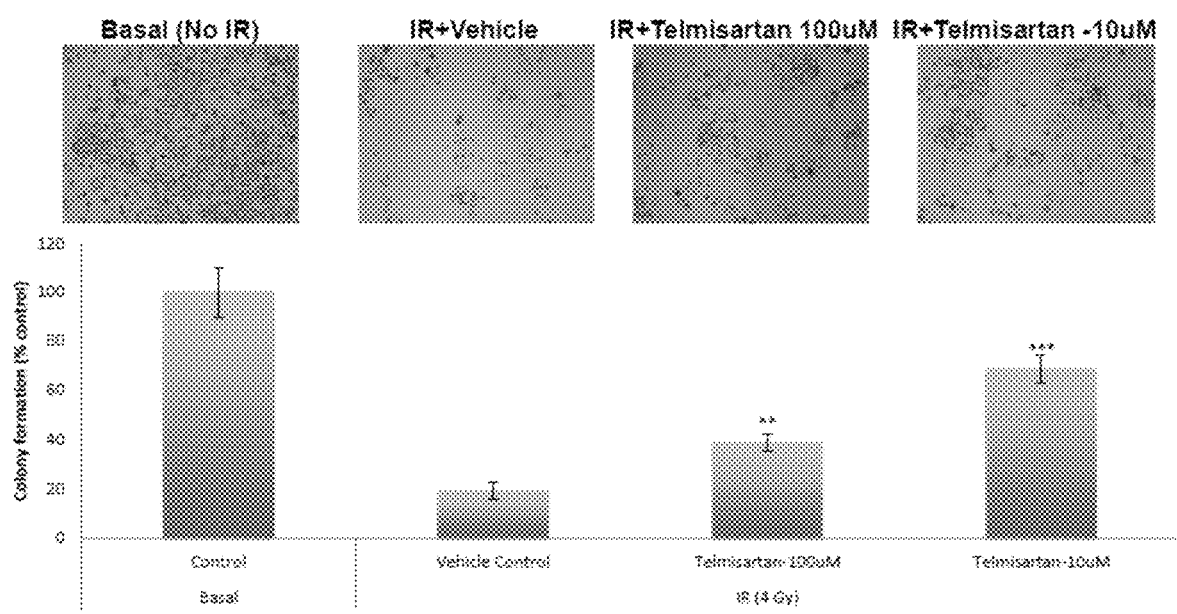
FIG. 1 is a series of photomicrographs and a related bar graph depicting the effect of telmisartan treatment on non-tumorigenic Young Adult Murine Colonic (YAMC) epithelial cell survival in vitro after 4 Gy ionizing radiation (IR). Cells in the treatment group received telmisartan 24 h post IR.

Before describing various embodiments of the compounds, compositions and methods of the present disclosure in more detail by way of exemplary description, examples, and results, it is to be understood that the compounds, compositions, and methods of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compounds, compositions, and methods of production and application and use thereof disclosed herein can be made and executed without undue experimentation in light of the present disclosure. Thus, while the compounds, compositions, and methods of the present disclosure have been described in terms of particular embodiments, it will be apparent to those of skill in the art that variations may be applied to the compounds, compositions and/or methods and in the steps or in the sequence of steps of the methods described herein without departing from the spirit, and scope of the inventive concepts.

All patents, published patent applications, and non-patent publications mentioned in the specification or referenced in any portion of this application are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

The term "pharmaceutically acceptable" refers to compounds and compositions which are suitable for administration to humans and/or animals without undue adverse side effects such as toxicity, irritation and/or allergic response commensurate with a reasonable benefit/risk ratio. The compounds of the present disclosure may be combined with one or more pharmaceutically-acceptable excipients, including carriers, vehicles, and diluents which may improve solubility, deliverability, dispersion, stability, and/or conformational integrity of the compounds or conjugates thereof.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The term "effective amount" refers to an amount of an active agent which is sufficient to exhibit a detectable therapeutic or treatment effect in a subject without excessive adverse side effects (such as substantial toxicity, irritation and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

Telmisartan (Micardis®, Boehringer Ingelheim) is an angiotensin II (Ang II) receptor antagonist (angiotensin receptor blocker; ARB) used for the management of hypertension. Telmisartan has high affinity for the angiotensin II receptor type 1 ($AT_1$), with a binding affinity 3000 times greater for $AT_1$ than for $AT_2$. It has the longest half-life of any ARB (24 hours) and the largest volume of distribution among ARBs (500 liters). In addition to blocking the angiotensin receptors, telmisartan acts as a selective modulator of peroxisome proliferator-activated receptor gamma (PPAR-γ), a central regulator of insulin and glucose metabolism. It is believed that telmisartan's dual mode of action may provide protective benefits against the vascular and renal damage caused by diabetes and cardiovascular disease.

Telmisartan is represented by formula II

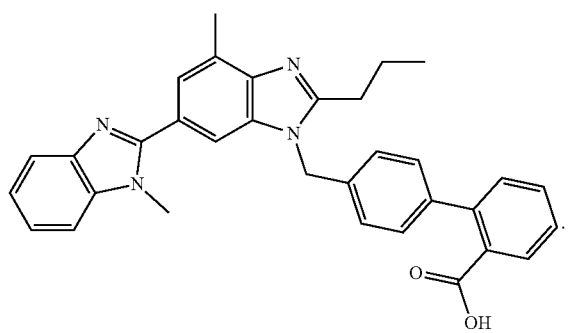

(II)

Tempol or 4-Hydroxy-TEMPO, formally 4-hydroxy-2,2,6,6-tetramethylpiperidin-1-oxyl, is a heterocyclic compound. Like the related TEMPO ((2,2,6,6-tetramethylpiperidin-1-yl)oxyl), it is used as a catalyst and chemical oxidant by virtue of being a stable radical. Tempol is recognized as an agent for detoxifying reactive oxygen species. It catalyzes the disproportionation of superoxide, facilitates hydrogen peroxide metabolism, and inhibit Fenton chemistry. Tempol is commercially available from any of a number of suppliers, e.g., Sigma-Aldrich.

Tempol is represented by formula III

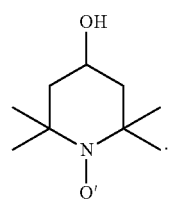

(III)

U.S. Pat. No. 9,233,949 to Brown et al. discloses an ester-linked conjugate formed between telmisartan and tempol. This conjugate, designated YK-4-250, is represented by:

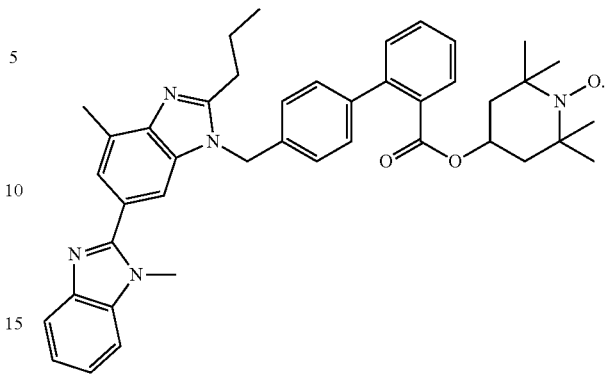

(YK-4-250)

YK-4-250 is disclosed in U.S. Pat. No. 9,233,949 to be useful to treat oxidative stress and/or hypertension by reducing Ang II-stimulated vascular superoxide ($O_2^-$) and blood pressure.

Exposure of living cells and tissue to high amounts of ionizing radiation causes physical damage or injury to cells and tissues. The damage or injury can include damage to DNA Acute radiation syndrome is typically caused by exposure to a large dose of ionizing radiation, e.g., for humans, greater than or equal to about 0.1 Gray (Gy), over a short period of time, e.g., one hour. Morbidity and mortality increase with absorbed dose. Acute radiation syndrome is also known as radiation poisoning, radiation sickness, and radiation toxicity.

Symptoms of acute radiation syndrome typically can include any one or more of nausea, vomiting, diarrhea, fever, headache, cognitive impairment, seizures, tremor, ataxia, lethargy, infection, anemia, and bleeding. Historically, at 6-8 Gy, mortality is 50-100 percent even with treatment, while at greater than 8 Gy, mortality is 100 percent even with treatment.

Methods

In at least one embodiment, the present disclosure is directed to a method for treating or preventing radiation-induced tissue injury, comprising administering to a subject in need thereof a therapeutically effective amount of a compound represented by formula I

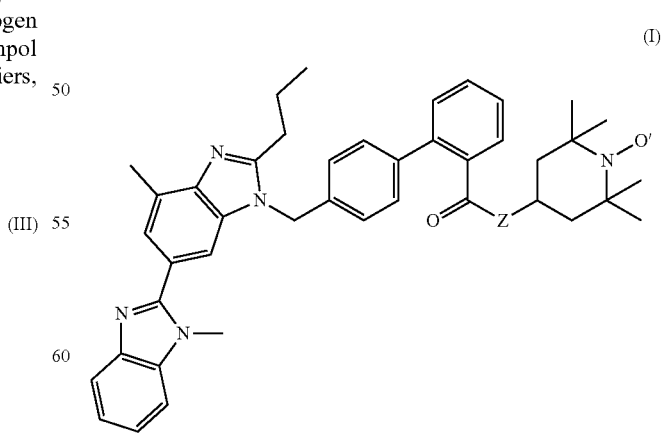

(I)

or a pharmaceutically acceptable salt thereof, wherein Z is —O— or —N(H)—, thereby treating or preventing radiation-induced tissue injury in the subject.

In certain embodiments, Z is —O— and the compound represented by formula I is

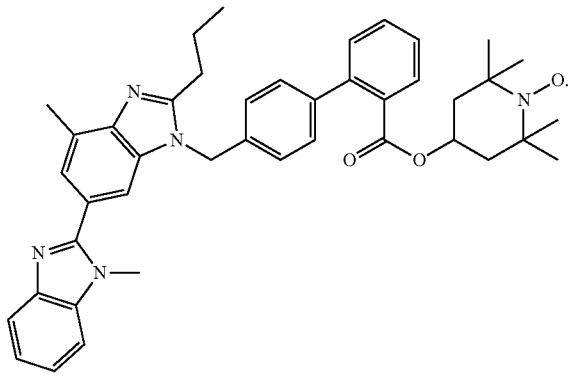

(YK-4-250)

In certain embodiments, Z is —N(H)—.

As used herein, "treat" means to reduce or mitigate at least one sign or symptom of an existing disease or condition of a subject. In certain embodiments, "treat" means to reduce or mitigate the severity of at least one sign or symptom of an existing disease or condition of a subject. In certain embodiments, "treat" means to reduce the duration of at least one sign or symptom of an existing disease or condition of a subject. In certain embodiments, "treat" means to resolve at least one sign or symptom of an existing disease or condition of a subject. In certain embodiments, "treat" means to restore the health of a subject, e.g., to restore to the health of the subject prior to the subject's development of the disease or condition. As used herein, "prevent" or "prevention" refers to prophylactic treatment measures to stop the onset of a condition or disease.

As used herein, "subject" refers to a living mammal. In certain embodiments, the subject is a mouse, rat, hamster, guinea pig, rabbit, sheep, goat, cat, dog, horse, cow, or non-human primate. In certain embodiments, the subject is a human.

As used herein, "radiation-induced tissue injury" refers to any injury or damage to cells of a tissue, where such injury or damage is consistent with or attributable to known exposure of the cells to ionizing radiation. The term "radiation-induced tissue injury" can refer to injury involving any one or more tissues, including acute radiation syndrome.

In certain embodiments, the radiation-induced tissue injury is prevented.

In certain embodiments, the radiation-induced tissue injury is treated.

In certain embodiments, the compound is administered prior to exposure of the subject to radiation. Such administration of the compound may then prevent or treat radiation-induced tissue injury in the subject. The agent administered in accordance with such embodiments can act both as a radioprotector and as a mitigator. For example, a subject about to embark on spaceflight or about to encounter a situation or environment known or believed to carry the risk of exposure to ionizing radiation may be administered the compound prior to said spaceflight or prior to encountering said situation or environment. The method is useful in settings including, but not limited to, nuclear disaster, accidental radiation exposure, acute radiation sickness, aviation, space travel, and protection of military personnel.

In certain embodiments, the compound is administered during exposure of the subject to radiation. Such administration of the compound may then prevent or treat radiation-induced tissue injury in the subject. The agent administered in accordance with such embodiments acts as a radioprotector and/or as a mitigator. The method is useful in settings including, but not limited to, nuclear disaster, accidental radiation exposure, acute radiation sickness, aviation, spaceflight and space travel, and treatment of military personnel.

In certain embodiments, the compound is administered after exposure of the subject to radiation. Such administration of the compound then treats radiation-induced tissue injury in the subject. The agent administered in accordance with such embodiments acts as a mitigator. The method is useful in settings including, but not limited to, nuclear disaster, accidental radiation exposure, acute radiation sickness, aviation, spaceflight and space travel, and treatment of military personnel.

In certain embodiments, the radiation-induced tissue injury is acute radiation-induced tissue injury.

In certain embodiments, the radiation-induced tissue injury is chronic radiation-induced tissue injury.

In certain embodiments, the tissue comprises gastrointestinal tissue. In certain embodiments, the tissue is gastrointestinal tissue. As used herein, "gastrointestinal tissue" refers generally to mouth, pharynx, esophagus, stomach, small intestine, large intestine, and rectum, including in particular epithelia lining said structures. In certain embodiments, "gastrointestinal tissue" refers to mouth, including in particular epithelia lining the mouth. In certain embodiments, "gastrointestinal tissue" refers to pharynx, including in particular epithelia lining the pharynx. In certain embodiments, "gastrointestinal tissue" refers to esophagus, including in particular epithelia lining the esophagus. In certain embodiments, "gastrointestinal tissue" refers to stomach, including in particular epithelia lining the stomach. In certain embodiments, "gastrointestinal tissue" refers to small intestine, including in particular epithelia lining the small intestine. In certain embodiments, "gastrointestinal tissue" refers to large intestine, including in particular epithelia lining the large intestine. In certain embodiments, "gastrointestinal tissue" refers to rectum, including in particular epithelia lining the rectum.

In certain embodiments, the tissue comprises hematopoietic tissue. In certain embodiments, the tissue is hematopoietic tissue. As used herein, "hematopoietic tissue" refers generally to blood cell-forming components of bone marrow. In certain embodiments, "hematopoietic tissue" refers to red blood cell-forming components of bone marrow. In certain embodiments, "hematopoietic tissue" refers to white blood cell-forming components of bone marrow. In certain embodiments, "hematopoietic tissue" also refers to thymus. In certain embodiments, "hematopoietic tissue" also refers to lymph nodes. In certain embodiments, "hematopoietic tissue" also refers to spleen. In certain embodiments, "hematopoietic tissue" also refers to liver.

In certain embodiments, the tissue comprises neural tissue. In certain embodiments, the tissue is neural tissue. As used herein, "neural tissue" refers generally to neurons of the central nervous system and peripheral nerves. In certain embodiments, "neural tissue" refers to neurons of the central nervous system. In certain embodiments, "neural tissue" refers to neurons of the brain. In certain embodiments, "neural tissue" refers to neurons of the spinal cord. In certain embodiments, "neural tissue" refers to neurons of peripheral nerves.

In certain embodiments, the tissue is selected from the group consisting of skin, eye, thyroid, heart, lung, kidney, adrenal gland, pancreas, gall bladder, breast, prostate, ovary, testis, uterus, vagina, and vascular tissue.

In certain embodiments, the compound is administered orally.

In certain embodiments, the compound is administered parenterally.

In at least one embodiment, the present disclosure is directed to a method for treating or preventing radiation-induced tissue injury, comprising administering to a subject in need thereof a therapeutically effective amount of a compound represented by formula II (telmisartan)

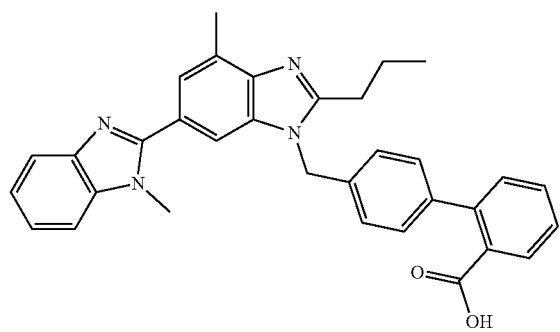

(II)

or a pharmaceutically acceptable salt thereof, thereby treating or preventing radiation-induced tissue injury in the subject.

In certain embodiments, the subject is a mouse, rat, hamster, guinea pig, rabbit, sheep, goat, cat, dog, horse, cow, or non-human primate. In certain embodiments, the subject is a human.

In certain embodiments, the radiation-induced tissue injury is prevented.

In certain embodiments, the radiation-induced tissue injury is treated.

In certain embodiments, the compound is administered prior to exposure of the subject to radiation. Such administration of the compound may then prevent or treat radiation-induced tissue injury in the subject. The administered agent in accordance with such embodiments can act both as a radioprotector and as a mitigator. For example, a subject about to embark on spaceflight or about to encounter a situation or environment known or believed to carry the risk of exposure to ionizing radiation may be administered the compound prior to said spaceflight or encountering said situation or environment. The method is useful in settings including, but not limited to, nuclear disaster, accidental radiation exposure, acute radiation sickness, aviation, space travel, and protection of military personnel.

In certain embodiments, the compound is administered during exposure of the subject to radiation. Such administration of the compound may then prevent or treat radiation-induced tissue injury in the subject. The agent administered in accordance with such embodiments acts as a radioprotector and/or as a mitigator. The method is useful in settings including, but not limited to, nuclear disaster, accidental radiation exposure, acute radiation sickness, aviation, spaceflight and space travel, and treatment of military personnel.

In certain embodiments, the compound is administered after exposure of the subject to radiation. Such administration of the compound then treats radiation-induced tissue injury in the subject. The administered agent in accordance with such embodiments acts as a mitigator. The method is useful in settings including, but not limited to, nuclear disaster, accidental radiation exposure, acute radiation sickness, aviation, spaceflight and space travel, and treatment of military personnel.

In certain embodiments, the radiation-induced tissue injury is acute radiation-induced tissue injury.

In certain embodiments, the radiation-induced tissue injury is chronic radiation-induced tissue injury.

In certain embodiments, the tissue comprises gastrointestinal tissue. In certain embodiments, the tissue is gastrointestinal tissue. In certain embodiments, "gastrointestinal tissue" refers to mouth, including in particular epithelia lining the mouth. In certain embodiments, "gastrointestinal tissue" refers to pharynx, including in particular epithelia lining the pharynx. In certain embodiments, "gastrointestinal tissue" refers to esophagus, including in particular epithelia lining the esophagus. In certain embodiments, "gastrointestinal tissue" refers to stomach, including in particular epithelia lining the stomach. In certain embodiments, "gastrointestinal tissue" refers to small intestine, including in particular epithelia lining the small intestine. In certain embodiments, "gastrointestinal tissue" refers to large intestine, including in particular epithelia lining the large intestine. In certain embodiments, "gastrointestinal tissue" refers to rectum, including in particular epithelia lining the rectum.

In certain embodiments, the tissue comprises hematopoietic tissue. In certain embodiments, the tissue is hematopoietic tissue. In certain embodiments, "hematopoietic tissue" refers to red blood cell-forming components of bone marrow. In certain embodiments, "hematopoietic tissue" refers to white blood cell-forming components of bone marrow. In certain embodiments, "hematopoietic tissue" also refers to thymus. In certain embodiments, "hematopoietic tissue" also refers to lymph nodes. In certain embodiments, "hematopoietic tissue" also refers to spleen. In certain embodiments, "hematopoietic tissue" also refers to liver.

In certain embodiments, the tissue comprises neural tissue. In certain embodiments, the tissue is neural tissue. In certain embodiments, "neural tissue" refers to neurons of the central nervous system. In certain embodiments, "neural tissue" refers to neurons of the brain. In certain embodiments, "neural tissue" refers to neurons of the spinal cord. In certain embodiments, "neural tissue" refers to neurons of peripheral nerves.

In certain embodiments, the tissue is selected from the group consisting of skin, eye, thyroid, heart, lung, kidney, adrenal gland, pancreas, gall bladder, breast, prostate, ovary, testis, uterus, vagina, and vascular tissue.

In certain embodiments, the compound is administered orally.

In certain embodiments, the compound is administered parenterally.

In at least one embodiment, the present disclosure is directed to a method for treating or preventing radiation-induced tissue injury, comprising administering to a subject in need thereof a therapeutically effective amount of a compound represented by formula III (tempol)

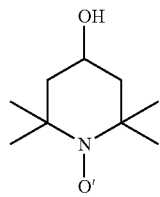

(III)

or a pharmaceutically acceptable salt thereof, to treat or prevent radiation-induced tissue injury in the subject.

In certain embodiments, the subject is a mouse, rat, hamster, guinea pig, rabbit, sheep, goat, cat, dog, horse, cow, or non-human primate. In certain embodiments, the subject is a human.

In certain embodiments, the radiation-induced tissue injury is prevented.

In certain embodiments, the radiation-induced tissue injury is treated.

In certain embodiments, the compound is administered prior to exposure of the subject to radiation. Such administration of the compound may then prevent or treat radiation-induced tissue injury in the subject. The administered agent in accordance with such embodiments can act both as a radioprotector and as a mitigator. For example, a subject about to embark on spaceflight or about to encounter a situation or environment known or believed to carry the risk of exposure to ionizing radiation may be administered the compound prior to said spaceflight or encountering said situation or environment. The method is useful in settings including, but not limited to, nuclear disaster, accidental radiation exposure, acute radiation sickness, aviation, space travel, and protection of military personnel.

In certain embodiments, the compound is administered during exposure of the subject to radiation. Such administration of the compound may then prevent or treat radiation-induced tissue injury in the subject. The agent administered in accordance with such embodiments acts as a radioprotector and/or as a mitigator. The method is useful in settings including, but not limited to, nuclear disaster, accidental radiation exposure, acute radiation sickness, aviation, spaceflight and space travel, and treatment of military personnel.

In certain embodiments, the compound is administered after exposure of the subject to radiation. Such administration of the compound then treats radiation-induced tissue injury in the subject. The administered agent in accordance with such embodiments acts as a mitigator. The method is useful in settings including, but not limited to, nuclear disaster, accidental radiation exposure, acute radiation sickness, aviation, spaceflight and space travel, and treatment of military personnel.

In certain embodiments, the radiation-induced tissue injury is acute radiation-induced tissue injury.

In certain embodiments, the radiation-induced tissue injury is chronic radiation-induced tissue injury.

In certain embodiments, the tissue comprises gastrointestinal tissue. In certain embodiments, the tissue is gastrointestinal tissue. In certain embodiments, "gastrointestinal tissue" refers to mouth, including in particular epithelia lining the mouth. In certain embodiments, "gastrointestinal tissue" refers to pharynx, including in particular epithelia lining the pharynx. In certain embodiments, "gastrointestinal tissue" refers to esophagus, including in particular epithelia lining the esophagus. In certain embodiments, "gastrointestinal tissue" refers to stomach, including in particular epithelia lining the stomach. In certain embodiments, "gastrointestinal tissue" refers to small intestine, including in particular epithelia lining the small intestine. In certain embodiments, "gastrointestinal tissue" refers to large intestine, including in particular epithelia lining the large intestine. In certain embodiments, "gastrointestinal tissue" refers to rectum, including in particular epithelia lining the rectum.

In certain embodiments, the tissue comprises hematopoietic tissue. In certain embodiments, the tissue is hematopoietic tissue. In certain embodiments, "hematopoietic tissue" refers to red blood cell-forming components of bone marrow. In certain embodiments, "hematopoietic tissue" refers to white blood cell-forming components of bone marrow. In certain embodiments, "hematopoietic tissue" also refers to thymus. In certain embodiments, "hematopoietic tissue" also refers to lymph nodes. In certain embodiments, "hematopoietic tissue" also refers to spleen. In certain embodiments, "hematopoietic tissue" also refers to liver.

In certain embodiments, the tissue comprises neural tissue. In certain embodiments, the tissue is neural tissue. In certain embodiments, "neural tissue" refers to neurons of the central nervous system. In certain embodiments, "neural tissue" refers to neurons of the brain. In certain embodiments, "neural tissue" refers to neurons of the spinal cord. In certain embodiments, "neural tissue" refers to neurons of peripheral nerves.

In certain embodiments, the tissue is selected from the group consisting of skin, eye, thyroid, heart, lung, kidney, adrenal gland, pancreas, gall bladder, breast, prostate, ovary, testis, uterus, vagina, and vascular tissue.

In certain embodiments, the compound is administered orally.

In certain embodiments, the compound is administered parenterally.

In at least one embodiment, the present disclosure is directed to a method for treating or preventing radiation-induced tissue injury, comprising co-administering to a subject in need thereof a therapeutically effective amount of a compound represented by formula II

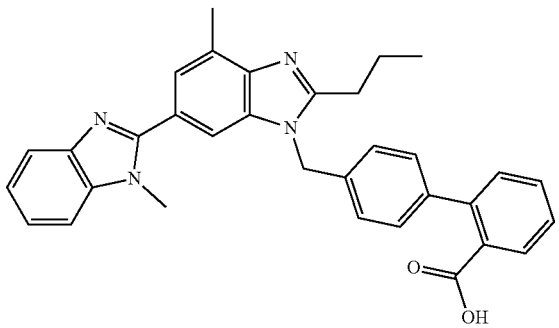

(II)

or a pharmaceutically acceptable salt thereof, and a therapeutically effective amount of a compound represented by formula III

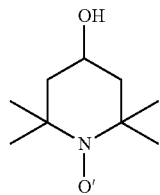

(III)

or a pharmaceutically acceptable salt thereof, thereby treating or preventing radiation-induced tissue injury in the subject.

As used herein, "co-administering" refers to administering a plurality of agents to a subject such that each of the plurality of agents is present in the subject simultaneously. In certain embodiments, agents are included in a single dosage form. In certain embodiments, the agents are administered simultaneously in separate dosage forms. In certain embodiments, the agents are administered sequentially in separate dosage forms.

In certain embodiments, the subject is a mouse, rat, hamster, guinea pig, rabbit, sheep, goat, cat, dog, horse, cow, or non-human primate. In certain embodiments, the subject is a human.

In certain embodiments, the radiation-induced tissue injury is prevented.

In certain embodiments, the radiation-induced tissue injury is treated.

In certain embodiments, the compounds are co-administered prior to exposure of the subject to radiation. Such co-administration of the compounds may then prevent or treat radiation-induced tissue injury in the subject. The co-administered agents in accordance with such embodiments can act both as radioprotectors and as mitigators. For example, a subject about to embark on spaceflight or about to encounter a situation or environment known or believed to carry the risk of exposure to ionizing radiation may be co-administered the compounds prior to said spaceflight or encountering said situation or environment. The method is useful in settings including, but not limited to, nuclear disaster, accidental radiation exposure, acute radiation sickness, aviation, space travel, and protection of military personnel.

In certain embodiments, the compounds are co-administered during exposure of the subject to radiation. Such co-administration of the compounds may then prevent or treat radiation-induced tissue injury in the subject. The agents co-administered in accordance with such embodiments act as radioprotectors and/or as mitigators. The method is useful in settings including, but not limited to, nuclear disaster, accidental radiation exposure, acute radiation sickness, aviation, spaceflight and space travel, and treatment of military personnel.

In certain embodiments, the compounds are co-administered after exposure of the subject to radiation. Such co-administration of the compounds then treats radiation-induced tissue injury in the subject. The co-administered agents in accordance with such embodiments act as mitigators. The method is useful in settings including, but not limited to, nuclear disaster, accidental radiation exposure, acute radiation sickness, aviation, spaceflight and space travel, and treatment of military personnel.

In certain embodiments, the radiation-induced tissue injury is acute radiation-induced tissue injury.

In certain embodiments, the radiation-induced tissue injury is chronic radiation-induced tissue injury.

In certain embodiments, the tissue comprises gastrointestinal tissue. In certain embodiments, the tissue is gastrointestinal tissue. In certain embodiments, "gastrointestinal tissue" refers to mouth, including in particular epithelia lining the mouth. In certain embodiments, "gastrointestinal tissue" refers to pharynx, including in particular epithelia lining the pharynx. In certain embodiments, "gastrointestinal tissue" refers to esophagus, including in particular epithelia lining the esophagus. In certain embodiments, "gastrointestinal tissue" refers to stomach, including in particular epithelia lining the stomach. In certain embodiments, "gastrointestinal tissue" refers to small intestine, including in particular epithelia lining the small intestine. In certain embodiments, "gastrointestinal tissue" refers to large intestine, including in particular epithelia lining the large intestine. In certain embodiments, "gastrointestinal tissue" refers to rectum, including in particular epithelia lining the rectum.

In certain embodiments, the tissue comprises hematopoietic tissue. In certain embodiments, the tissue is hematopoietic tissue. In certain embodiments, "hematopoietic tissue" refers to red blood cell-forming components of bone marrow. In certain embodiments, "hematopoietic tissue" refers to white blood cell-forming components of bone marrow. In certain embodiments, "hematopoietic tissue" also refers to thymus. In certain embodiments, "hematopoietic tissue" also refers to lymph nodes. In certain embodiments, "hematopoietic tissue" also refers to spleen. In certain embodiments, "hematopoietic tissue" also refers to liver.

In certain embodiments, the tissue comprises neural tissue. In certain embodiments, the tissue is neural tissue. In certain embodiments, "neural tissue" refers to neurons of the central nervous system. In certain embodiments, "neural tissue" refers to neurons of the brain. In certain embodiments, "neural tissue" refers to neurons of the spinal cord. In certain embodiments, "neural tissue" refers to neurons of peripheral nerves.

In certain embodiments, the tissue is selected from the group consisting of skin, eye, thyroid, heart, lung, kidney, adrenal gland, pancreas, gall bladder, breast, prostate, ovary, testis, uterus, vagina, and vascular tissue.

In certain embodiments, the compounds are co-administered orally.

In certain embodiments, the compounds are co-administered parenterally.

In certain embodiments, the compounds are co-administered sequentially.

In certain embodiments, the compounds are co-administered substantially simultaneously.

Formulation and Dosing

Suitable routes of administration include, but not limited to, oral and parenteral. Suitable routes of parenteral administration may, for example, include intravenous, intraperitoneal, intramuscular, subcutaneous, rectal, transmucosal, topical, pulmonary, and intrathecal.

Alternatively, administration may be in a local rather than a systemic manner, for example, via injection of a compound directly into a specific anatomical site, often in a depot or sustained release formulation.

Furthermore, the administration may be in a targeted drug delivery system, for example, in a liposome coated with cell-specific antibody or other targeting agent.

The pharmaceutical compositions of the present disclosure may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present disclosure thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the active agent or agents used in the methods of the present disclosure may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the active agent or agents can be formulated readily by combining the active compounds with pharmaceutically acceptable carriers well known in the art. Such carriers enable the mixtures or adducts of the invention to be formulated as tablets, pills, dragees, capsules, liquids, gels, syrups, slurries, suspensions and the like, for oral ingestion by a subject to be treated. Pharmaceutical preparations for oral use can be obtained by combining the mixtures or adducts of the invention with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

In one embodiment the pharmaceutically acceptable carrier excludes dimethylsulfoxide (DMSO).

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the active agent or agents for use according to the present disclosure are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The active agent or agents of the invention can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the mixtures or adducts of the present disclosure may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active agent or agents of the present disclosure may be in powder form for constitution with a suitable vehicle, e.g., sterile pyrogen-free water, before use.

The active agent or agents of the present disclosure may also be formulated in rectal compositions such as suppositories or retention enemas, e.g., containing conventional suppository bases such as cocoa butter or other glycerides.

In addition to the formulations described previously, the active agent or agents of the present disclosure may also be formulated as a depot preparation. Such long acting formulations may be administered by implantation (for example subcutaneously or intramuscularly or by intramuscular injection). Thus, for example, the mixtures or adducts of the present disclosure may be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide (DMSO) also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Compounds for use according to the present disclosure may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di alkyl-N-(hydroxy alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Pharmaceutical compositions suitable for use in the present disclosure include compositions wherein each active agent is contained in an effective amount to achieve its intended purpose.

As used herein, a "therapeutically effective amount" is an amount which inhibits, totally or partially, the progression of a condition to be treated; or alleviates, at least partially, one or more symptoms of said condition. Alternatively or in addition, in certain embodiments a therapeutically effective amount can be an amount which is prophylactically effective. The amount which is therapeutically effective will depend upon factors such as the subject's size and gender, the condition to be treated, the severity of the condition and the result sought. For a given subject, a therapeutically effective amount can be determined by methods known to those of skill in the art.

In the methods of the invention the active agent or agents can be administered orally or by injection, using any pharmaceutical dosage forms known for the person skilled in the art for such administration. Dosing may be a single dose or multiple doses.

A manner of administration is oral administration.

For oral administration both solid and liquid formulations can be used. Solid formulations include conventional tablets, capsules, troches, powders or granulates for direct ingestion or for reconstitution in liquids, such as water or juices. Any suitable conventional excipients can be used for the preparation of such solid forms. Liquid forms for oral administration include in particular aqueous solutions, with the addition of any conventional excipients, such as for example flavors and/or sweeteners.

Another manner of administration is parenteral administration, especially by continuous infusion or a single bolus.

Administration by injection includes bolus intravenous injection, continuous intravenous infusion, as well as subcutaneous injection. Any suitable injection formulation can be used, such as for example aqueous saline solutions, buffered saline solutions, etc., using conventional excipients known from the art, such as preservatives, isotonic agents, buffers, etc.

The administration, in a single dose or in multiple doses, can be prior to or after a radiation exposure. In the case of multiple doses, administration can be continued in cycles, such as every day, every other day, or every several days. The administration can be continued for several days or weeks. In the case of long-term radiation exposure, the administration can be during the whole exposure period and can be continued after cessation of the exposure for several days or weeks.

Dosage can be based, at least in part, on results of in vitro testing and/or in vivo testing in laboratory animals, some methods for which are described in the examples below.

Actual dosage levels of the active agent or agents in the methods of the present disclosure may be varied so as to obtain an amount of the active ingredient which is effective to achieve the desired therapeutic response for a particular patient, composition, and mode of administration, preferably without being toxic to the patient.

Dosage regimen in the case of the administration as a protective measure in the case of routine, expected, or predictable long-term exposure to low-dose ionizing radiation can be in the range of about 1 mg/kg body weight to 100 mg/kg body weight of the active agent or agents per day. The active agent or agents can be administered as a protective measure before the onset to the exposure in one single dose, or alternatively in divided doses, during the period of such exposure and optionally for some period after cessation of the exposure. The administration can be preferably repeated daily.

In the case of expected acute exposure, such as for example the exposure of a professional rescue or emergency staff after accidents involving ionizing radiation, the active agent or agents should be administered prior the expected exposure, in one single dose or in multiple doses and preferably its administration should be continued for the whole period of exposure.

Dosage regimens in the case of administration as a part of a radiotherapy procedure can be in, but are not limited to, the range of about 2 mg/kg body weight to 200 mg/kg body weight of the active agent or agents in a single dose before irradiation, such as, but not limited to, 1 hour, 30 minutes, or 15 minutes before irradiation. In particular, dosages such as 5 mg/kg to 20 mg/kg can be used, or 5 mg/kg to 10 mg/kg. In certain embodiments, a dose of the active agent or agents is about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, or about 20 mg/kg.

In the case of accidental acute exposure, the active agent or agents should be administered to the victim of such accidental exposure as soon as possible after the exposure has taken place and typically should be continued daily for some period, such as several days or weeks, after the exposure. In such cases a dosage regimen of about, but not limited to, 2 mg/kg body weight to about 200 mg/kg body weight per day is contemplated, depending on the radiation dose absorbed by the subject, the route of administration, and/or the clinical condition of the subject.

Generally, the dose of the active agent or agents will vary depending on the absorbed or expected dose of the radiation. The selected dosage level will also depend upon a variety of factors including the activity of the particular active agent or agents employed, the time of administration, the rate of excretion of the particular active agent or agents being employed, the duration of the treatment, other drugs, compounds or materials used in combination with the particular active agent or agents, the age, sex, weight, condition, general health, and prior medical history of the patient being treated, and like factors well known in the medical arts.

A medical doctor, e.g., physician or veterinarian, having ordinary skill in the art can readily determine and prescribe the effective amount of the active agent or agents required. A medical doctor, e.g., physician or veterinarian, having ordinary skill in the art can readily determine and prescribe the effective amount of a pharmaceutical composition or pharmaceutical compositions comprising the active agent or agents required.

One of ordinary skill in the art would be able to study the relevant factors and make the determination regarding the effective amount of the active agent or agents without undue experimentation.

EXAMPLES

Having now described the several embodiments of the present disclosure in detail, the same will be more clearly understood by reference to the following examples, which are included herewith for purposes of illustration only and are not intended to be limiting of the present disclosure.

Example 1. Synthesis of Telmisartan/Tempol Conjugate (YK-4-250)

Analytical Methods. NMR spectra were recorded using a Varian-400 spectrometer for $^1$H (400 MHz). Chemical shifts (δ) are given in ppm downfield from tetramethylsilane, as internal standard, and coupling constants (J-values) are in hertz (Hz). Purifications by flash chromatography were performed. Liquid chromatography/mass spectrometry (LC/MS) analyses were conducted using Shimadzu LC-20AD pumps and a SPD-20A UV-vis detector. High-resolution mass spectra (HMRS) were recorded on a QSTAR Elite mass spectrometer.

Telmisartan Extraction. Telmisartan tablets were triturated, suspended in methanol and stirred for about 20 mins. Filtered off the solid, the methanol solution was concentrated, and the residue was purified by chromatography to afford white solid in 90% yield. $^1$H NMR (CDCl$_3$, 400 MHz) δ 8.38 (m, 1H), 8.02 (dd, 1H, J=1.2, 1.2 Hz), 7.39 (m, 8H), 7.17 (s, 1H), 7.15 (s, 1H), 7.04 (s, 1H), 6.95 (s, 1H), 5.40 (s, 2H), 3.74 (s, 3H), 3.13 (t, 2H, J=7.6, 8.0 Hz), 2.69 (s, 3H), 1.99 (m, 2H), 1.15 (t, 3H, J=7.6, 7.2 Hz).

Conjugation of Telmisartan with Tempol (YK-4-250).

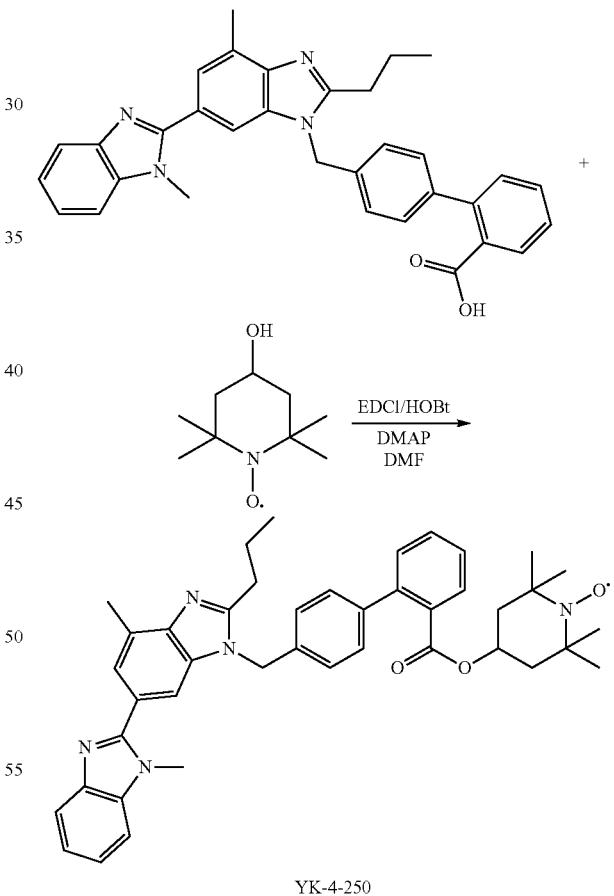

To an ice bath cooled solution of telmisartan (0.8 g, 1.55 mmol) in DMF (50 mL) was added 1-hydroxybenzotriazole (HOBt, 0.25 g, 1.87 mmol), 4-dimethylamino pyridine (DMAP, 0.23 g, 1.87 mmol), and 1-(3-dimethylaminopropyl)-3-ethylcarbodiimide hydrochloride (EDCI, 0.39 g, 2.02 mmol), followed by tempol (0.29 g, 1.712 mmol). The mixture was stirred at room temperature for 48 h. Water (15 mL) was added to the mixture and stirred at room temperature for 10 minutes. The mixture was extracted with ethyl acetate (3×15 mL). The organic layer was washed with sat. LiCl (15 mL), sat. NaHCO$_3$ (15 mL), water (15 mL) and brine (15 mL), dried over Na$_2$SO$_4$. The solvent was evaporated and the residue was purified by flash chromatography using CH$_2$Cl$_2$-MeOH to afford YK-4-250 as a pink soft solid (0.81 g, 78%). LC-MS (ESI): m/z 669 (M+H)$^+$; HRMS (TOF): calculated for C$_{42}$H$_{47}$N$_5$O$_3$ (M+H)$^+$: 669.3679; Found: 669.3578.

Example 2. In Vitro Protective Effects of Telmisartan

Gamma radiation: YAMC (normal colonic epithelial cell line) were exposed to 4 Gy gamma ionizing radiation (IR) with air pumped into the chamber during exposure. A Gammacell 40 $^{137}$Cs gamma irradiator was used with a dose rate of 0.8 Gy IR per minute. Dosimetry measurements were performed using Fricke Dosimetry systems. Measured absorbance dose was: Central Dose Rate (0.790 Gy/min±2.9%); 3 o'clock position (0.804 Gy/min±3.8%); and 7 o'clock position (0.808 Gy/min±2.7%). The experiments were performed within 6 months of the dosimetry analysis. YAMC cells in the treatment group received telmisartan 24 h post-IR at three different doses (10 µM, 100 µM, and 1 mM).

Colony forming assay: Colony forming assay is universally recognized as the gold standard method for measuring the effects of radiation, chemotherapeutic drugs on cell viability, and cell survival. 24 h post-IR YAMC cells were split into 6-well plates for colony formation assessment with and without telmisartan treatment. At the end of 96 h, cells were fixed and counted for number of colonies formed. The number of colonies formed represents the number of cells survived. Representative results are shown in FIG. 1. As shown in the figure, telmisartan treatment significantly increased YAMC cell survival compared to vehicle treatment after 4 Gy IR.

Figure 2:
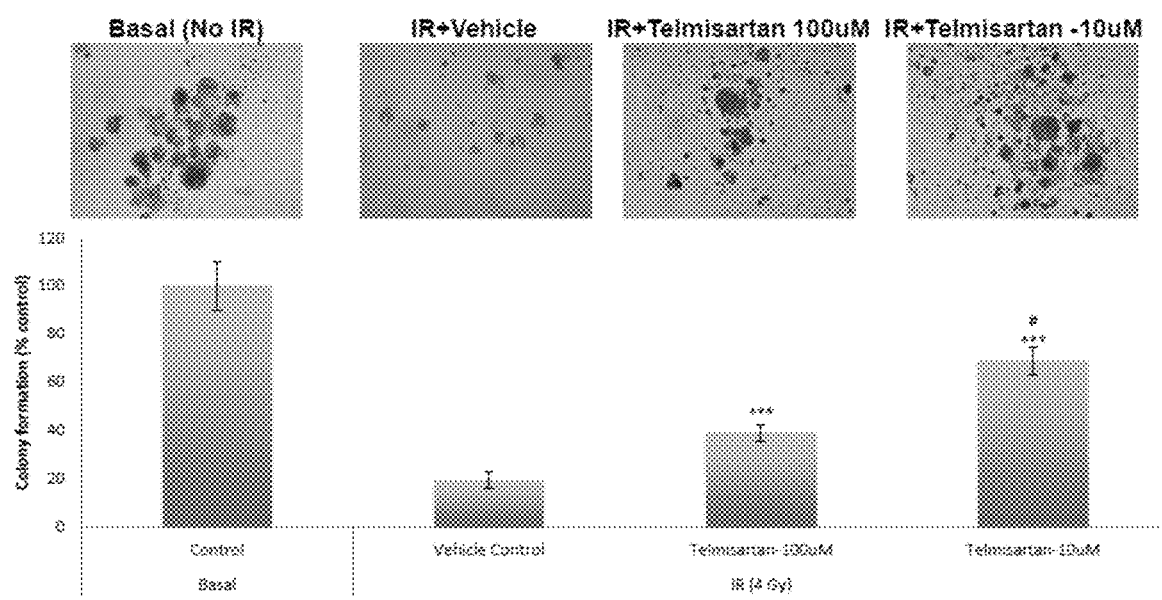
FIG. 2 is a series of photomicrographs and a related bar graph depicting the effect of telmisartan treatment on YAMC cell self-renewal in vitro after 4 Gy IR. Cells in the treatment group received telmisartan 24 h post IR.

Clonogenic assay for self-renewal: Self-renewal is the hallmark for stem cells or stem-like cells. Clonogenic assay or clonal expansion of single cell into spheroids/organoids is the reputed method to analyze cell self-renewal. 24 h post-IR YAMC cells were split into 96-well plates (ultra-low attachment plates) in spheroid growth conditioned media for self-renewal ability with and without telmisartan. At the end of 192 h, spheroids were counted for quantitative assessment of the number of spheroids formed. Representative results are shown in FIG. 2. As shown in the figure, telmisartan treatment significantly increased the self-renewal ability of YAMC cells compared to vehicle treatment after 4 Gy IR.

Example 3. In Vivo Protective Effects of Telmisartan

Gamma radiation: 7-week-old C57BL/6 mice were exposed to total body irradiation (TBI) 14 Gy gamma ionizing radiation (IR) with air pumped into the chamber during. A Gammacell 40 $^{137}$Cs gamma irradiator was used with a dose rate of 0.8 Gy IR per minute. Dosimetry measurements were performed using Fricke Dosimetry systems. Measured absorbance dose was: Central Dose Rate (0.790 Gy/min±2.9%); 3 o'clock position (0.804 Gy/min±3.8%); and 7 o'clock position (0.808 Gy/min±2.7%). The experiments were performed within 6 months of the dosimetry analysis. All IR treatments were begun in the morning. Animals in the treatment group received three doses of telmisartan, 10 mg/kg body weight per day, beginning 24 h post-IR. All animals received easy access to liquid gel food and water in the cage.

Crypt survival analysis: Two hours before euthanasia (82 h post-IR), each mouse was intraperitoneally injected with 5-bromo-2'-deoxyuridine (BrdUrd, Sigma Aldrich, St. Louis, Mo.; 200 µL of 5 mg/mL BrdUrd solution in PBS).

Figure 3:
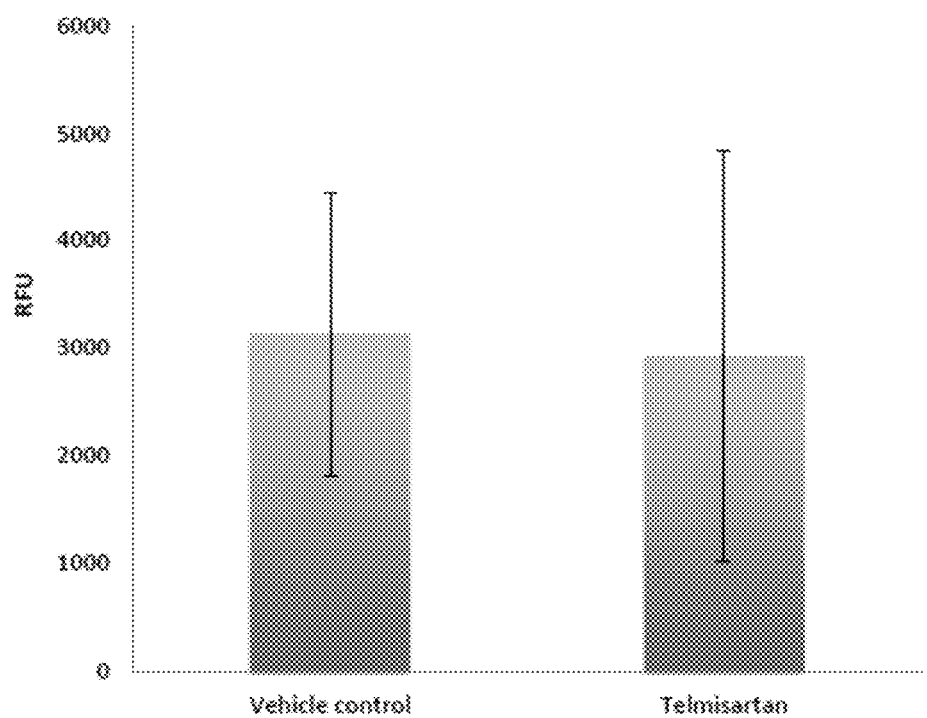
FIG. 3 is a bar graph depicting in vivo whole intestinal epithelial permeability to FITC-dextran 5 days after 14 Gy total body irradiation. Animals received three daily doses of either vehicle control or telmisartan beginning 24 h post-IR.

Barrier function study: Two hours before euthanasia (5 d post-IR), each mouse was orally administered (gavage) with 100 µL of FITC-dextran (FITC dextran 4; MW 4000) at a dose of 80 mg/100 g body weight. Serum analysis of FITC concentration was performed in triplicate using Synergy Bio TEK plate reader. Representative results are shown in FIG. 3. As shown in the figure, intestinal epithelial permeability to FITC-dextran was essentially the same for vehicle control and telmisartan groups.

Figure 4:
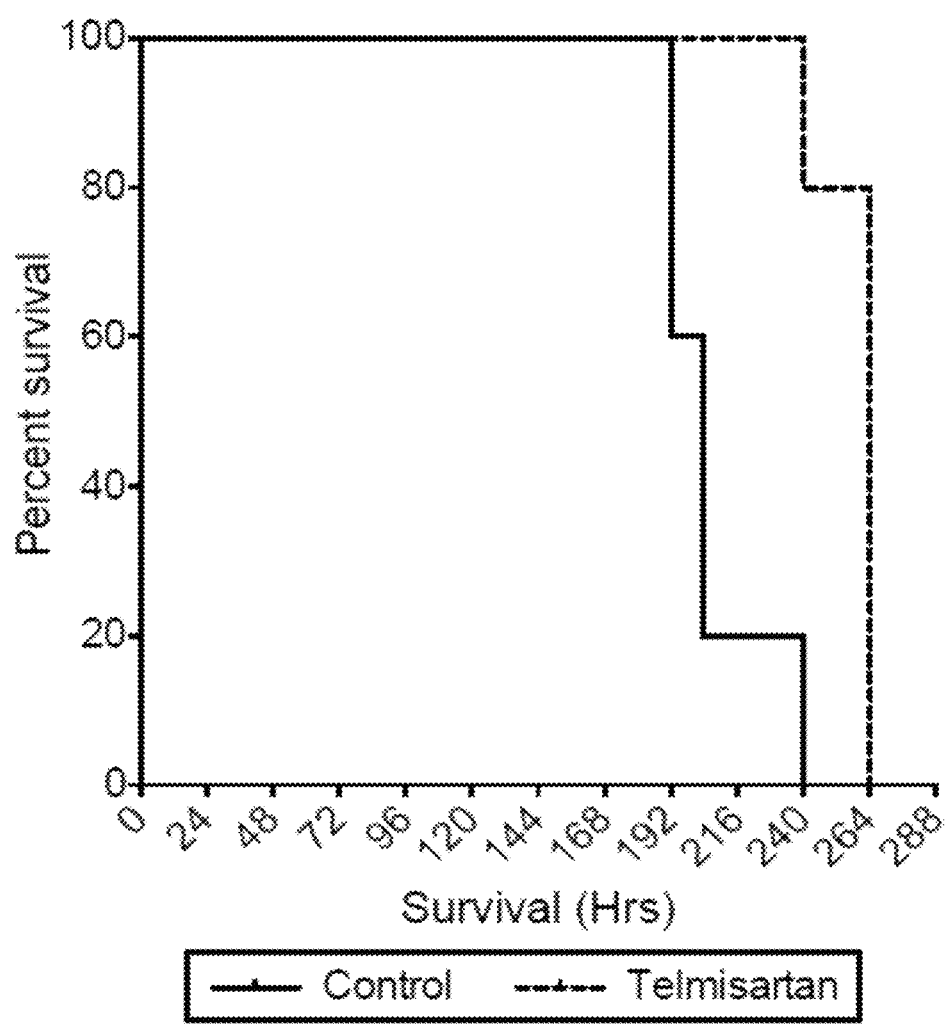
FIG. 4 is a graph depicting survival of mice following 14 Gy total body irradiation. Animals received three daily doses of either vehicle control or telmisartan beginning 24 h post-IR.

Overall survival study: Animals following treatment (IR and/or IR+telmisartan) were allowed to survive. Animals demonstrating bloody stools, lethargy, or unable to move were killed and time of death noted. Survival time of mice in the treatment group was compared with control IR-alone-treated mice. Representative results are shown in FIG. 4. As shown in the figure, median survival for control-treated mice was 204 days, whereas median survival for telmisartan-treated mice was 264 days. Log-rank (Mantel-Cox) test chi square 7.962; p=0.0048.

Example 4. In Vitro Protective Effects of Tempol

Gamma radiation: YAMC (normal colonic epithelial cell line) were exposed to 4 Gy gamma ionizing radiation (IR) with air pumped into the chamber during exposure. A Gammacell 40 $^{137}$Cs gamma irradiator was used with a dose rate of 0.8 Gy IR per minute. Dosimetry measurements were performed using Fricke Dosimetry systems. Measured absorbance dose was: Central Dose Rate (0.790 Gy/min±2.9%); 3 o'clock position (0.804 Gy/min±3.8%); and 7 o'clock position (0.808 Gy/min±2.7%). The experiments were performed within 6 months of the dosimetry analysis. YAMC cells in the treatment group received tempol 24 h post-IR at three different doses (10 µM, 100 µM, and 1 mM).

Figure 5:
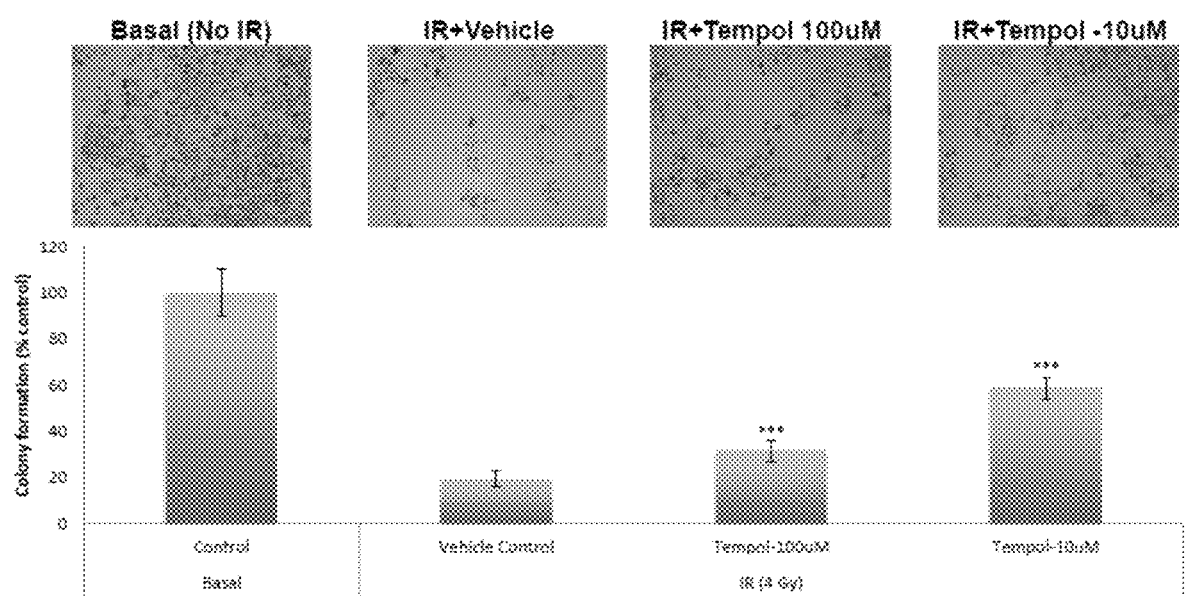
FIG. 5 is a series of photomicrographs and a related bar graph depicting the effect of tempol treatment on YAMC cell survival in vitro after 4 Gy IR. Cells in the treatment group received tempol 24 h post IR.

Colony forming assay: Colony forming assay is universally recognized as the gold standard method for measuring the effects of radiation, chemotherapeutic drugs on cell viability, and cell survival. 24 h post-IR YAMC cells were split into 6-well plates for colony formation assessment with and without tempol treatment. At the end of 96 h, cells were fixed and counted for number of colonies formed. The number of colonies formed represents the number of cells survived. Representative results are shown in FIG. 5. As shown in the figure, tempol treatment significantly increased YAMC cell survival compared to vehicle treatment after 4 Gy IR.

Figure 6:
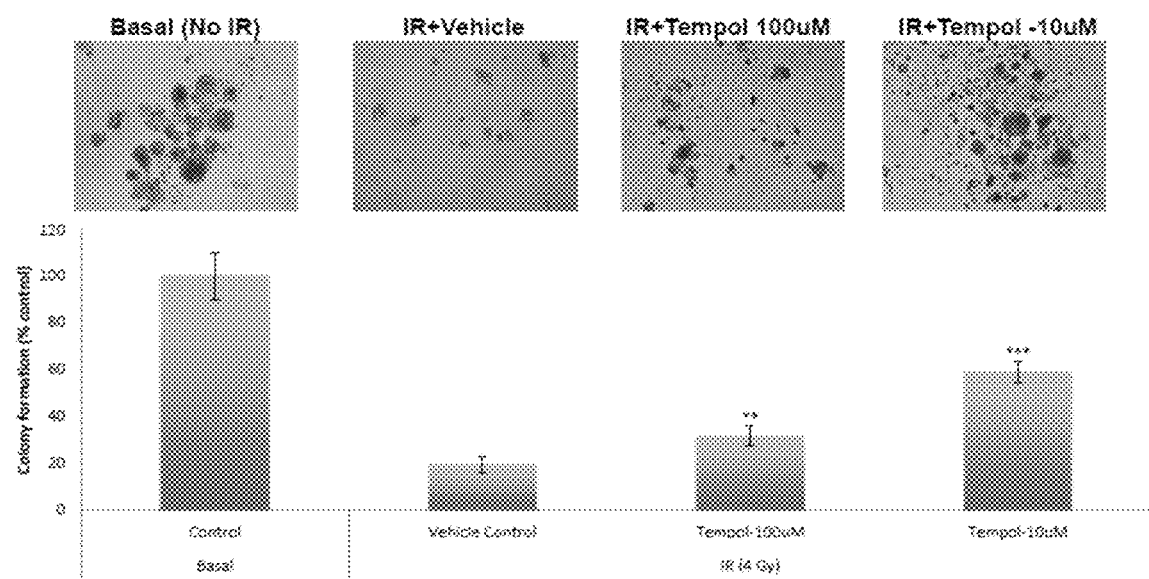
FIG. 6 is a series of photomicrographs and a related bar graph depicting the effect of tempol treatment on YAMC cell self-renewal in vitro after 4 Gy IR. Cells in the treatment group received tempol 24 h post IR.

Clonogenic assay for self-renewal: Self-renewal is the hallmark for stem cells or stem-like cells. Clonogenic assay or clonal expansion of single cell into spheroids/organoids is the reputed method to analyze cell self-renewal. 24 h post-IR YAMC cells were split into 96-well plates (ultra-low attachment plates) in spheroid growth conditioned media for self-renewal ability with and without tempol. At the end of 192 h, spheroids were counted for quantitative assessment of the number of spheroids formed. Representative results are shown in FIG. 6. As shown in the figure, tempol treatment significantly increased the self-renewal ability of YAMC cells compared to vehicle treatment after 4 Gy IR.

Example 5. In Vivo Protective Effects of Tempol

Gamma radiation: 7-week-old C57BL/6 mice were exposed to total body irradiation (TBI) 14 Gy gamma ionizing radiation (IR) with air pumped into the chamber during. A Gammacell 40 $^{137}$Cs gamma irradiator was used with a dose rate of 0.8 Gy IR per minute. Dosimetry measurements were performed using Fricke Dosimetry systems. Measured absorbance dose was: Central Dose Rate (0.790 Gy/min±2.9%); 3 o'clock position (0.804 Gy/min±3.8%); and 7 o'clock position (0.808 Gy/min±2.7%). The experiments were performed within 6 months of the dosimetry analysis. All IR treatments were begun in the morning. Animals in the treatment group received three doses of tempol, 10 mg/kg body weight per day, beginning 24 h post-IR. All animals received easy access to liquid gel food and water in the cage.

Crypt survival analysis: Two hours before euthanasia (82 h post-IR), each mouse was intraperitoneally injected with 5-bromo-2'-deoxyuridine (BrdUrd, Sigma Aldrich, St. Louis, Mo.; 200 µL of 5 mg/mL BrdUrd solution in PBS).

Figure 7:
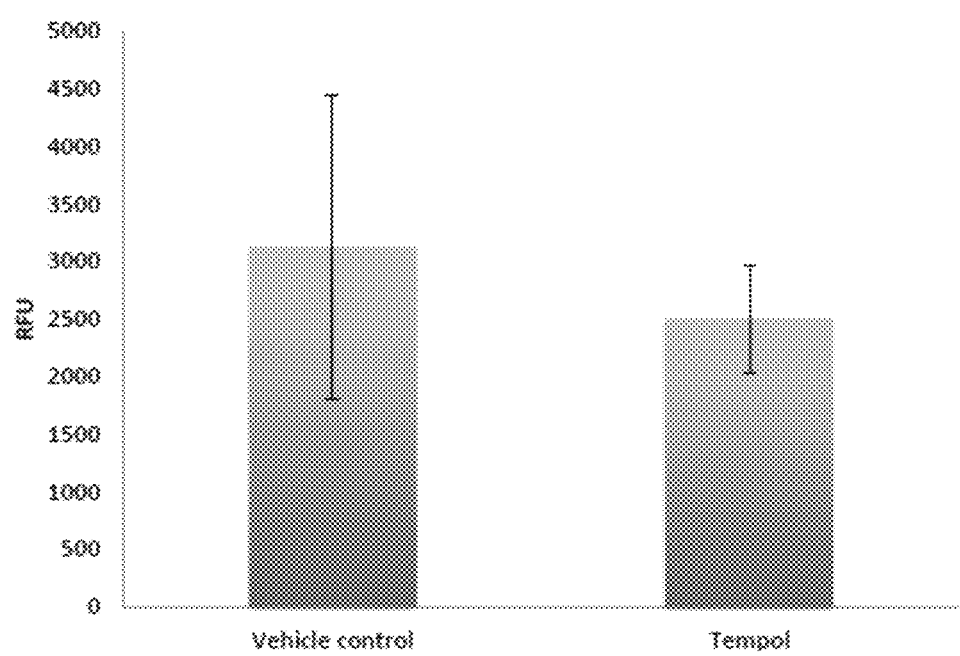
FIG. 7 is a bar graph depicting in vivo whole intestinal epithelial permeability to FITC-dextran 5 days after 14 Gy total body irradiation. Animals received three daily doses of either vehicle control or tempol beginning 24 h post-IR.

Barrier function study: Two hours before euthanasia (5 d post-IR), each mouse was orally administered (gavage) with 100 µL of FITC-dextran (FITC dextran 4; MW 4000) at a dose of 80 mg/100 g body weight. Serum analysis of FITC concentration was performed in triplicate using Synergy Bio TEK plate reader. Representative results are shown in FIG. 7. As shown in the figure, intestinal epithelial permeability to FITC-dextran was essentially the same for vehicle control and tempol groups.

Figure 8:
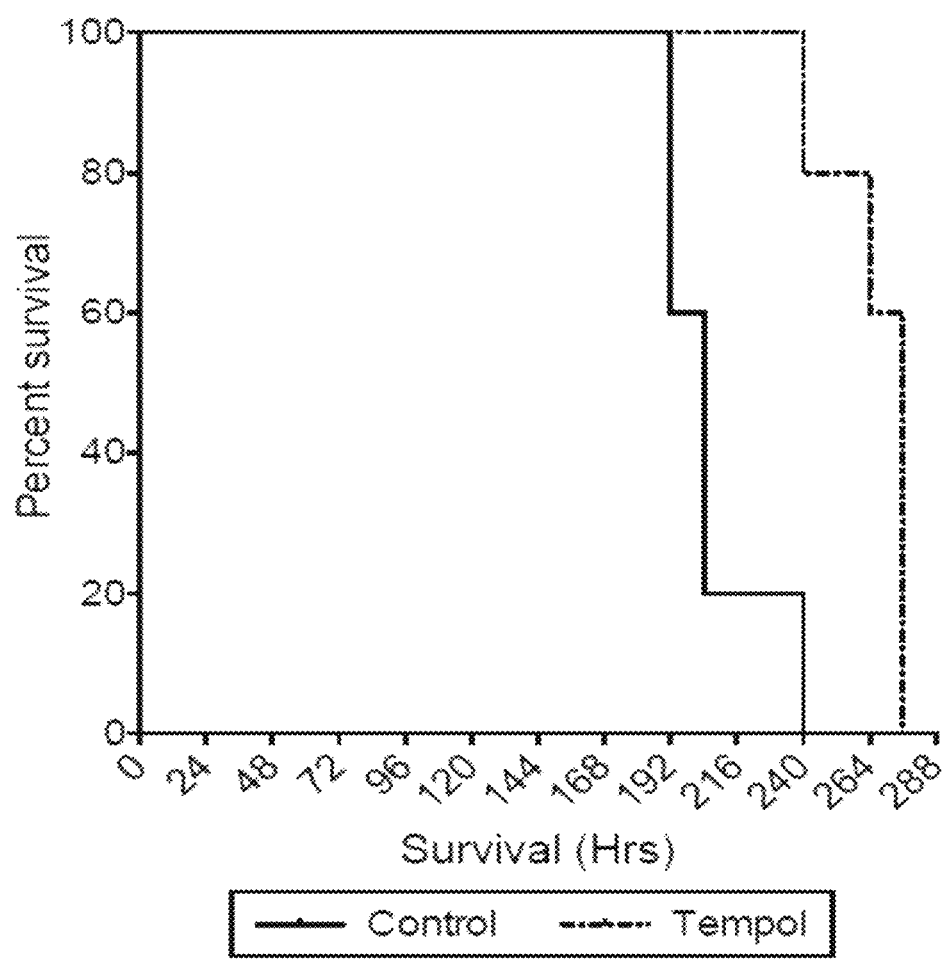
FIG. 8 is a graph depicting survival of mice following 14 Gy total body irradiation. Animals received three daily doses of either vehicle control or tempol beginning 24 h post-IR.

Overall survival study: Animals following treatment (IR and/or IR+tempol) were allowed to survive. Animals demonstrating bloody stools, lethargy, or unable to move were killed and time of death noted. Survival time of mice in the treatment group was compared with control IR-alone-treated mice. Representative results are shown in FIG. 8. As shown in the figure, median survival for control-treated mice was 204 days, whereas median survival for tempol-treated mice was 276 days. Log-rank (Mantel-Cox) test chi square 7.962; p=0.0048.

Example 6. In Vitro Protective Effects of YK-4-250

Gamma radiation: YAMC (normal colonic epithelial cell line) were exposed to 4 Gy gamma ionizing radiation (IR) with air pumped into the chamber during exposure. A Gammacell 40 $^{137}$Cs gamma irradiator was used with a dose rate of 0.8 Gy IR per minute. Dosimetry measurements were performed using Fricke Dosimetry systems. Measured absorbance dose was: Central Dose Rate (0.790 Gy/min±2.9%); 3 o'clock position (0.804 Gy/min±3.8%); and 7 o'clock position (0.808 Gy/min±2.7%). The experiments were performed within 6 months of the dosimetry analysis. YAMC cells in the treatment group received YK-4-250 24 h post-IR at three different doses (10 µM, 100 µM, and 1 mM).

Figure 9:
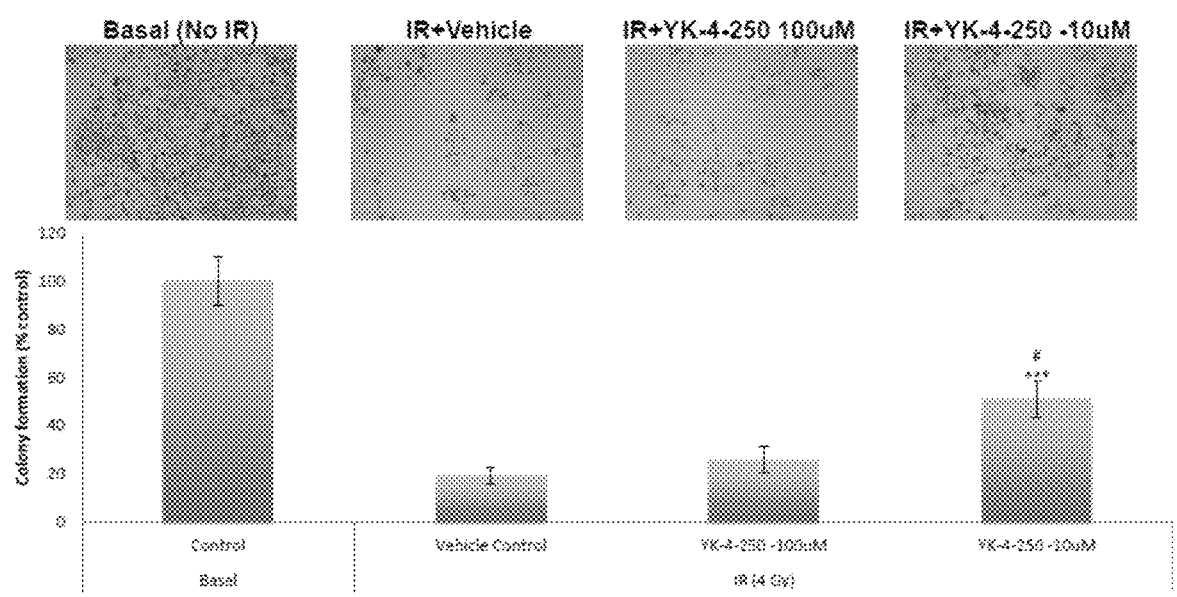
FIG. 9 is a series of photomicrographs and a related bar graph depicting the effect of YK-4-250 treatment on YAMC cell survival in vitro after 4 Gy IR. Cells in the treatment group received YK-4-250 24 h post IR.

Colony forming assay: Colony forming assay is universally recognized as the gold standard method for measuring the effects of radiation, chemotherapeutic drugs on cell viability, and cell survival. 24 h post-IR YAMC cells were split into 6-well plates for colony formation assessment with and without YK-4-250 treatment. At the end of 96 h, cells were fixed and counted for number of colonies formed. The number of colonies formed represents the number of cells survived. Representative results are shown in FIG. 9. As shown in the figure, YK-4-250 treatment significantly increased YAMC cell survival compared to vehicle treatment after 4 Gy IR.

Figure 10:
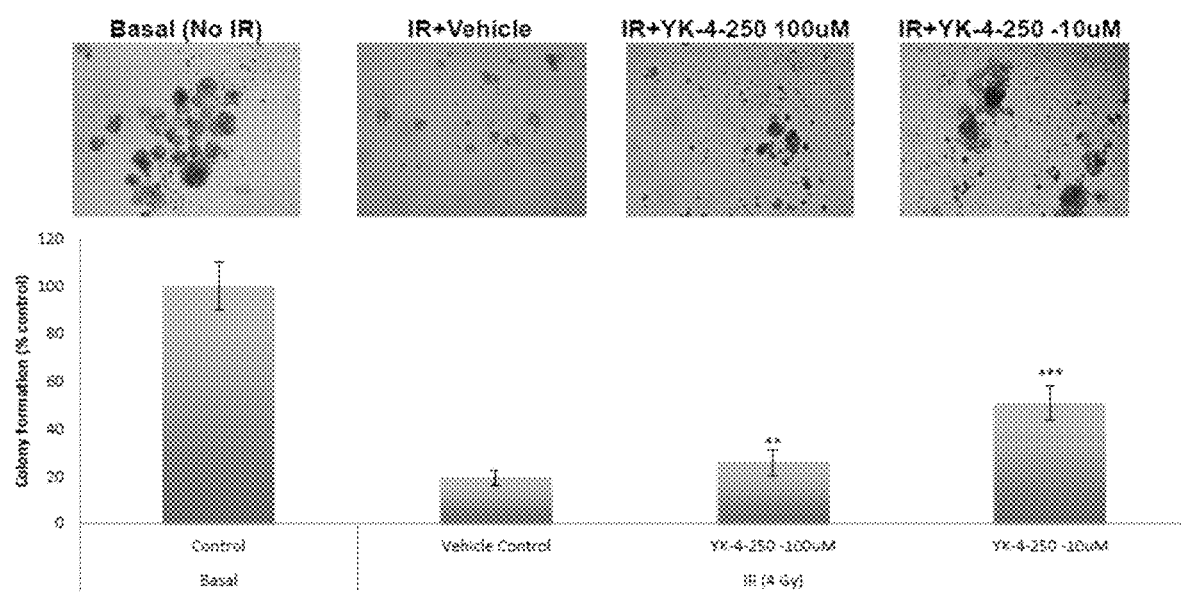
FIG. 10 is a series of photomicrographs and a related bar graph depicting the effect of tempol treatment on YAMC cell self-renewal in vitro after 4 Gy IR. Cells in the treatment group received YK-2-250 24 h post IR.

Clonogenic assay for self-renewal: Self-renewal is the hallmark for stem cells or stem-like cells. Clonogenic assay or clonal expansion of single cell into spheroids/organoids is the reputed method to analyze cell self-renewal. 24 h post-IR YAMC cells were split into 96-well plates (ultra-low attachment plates) in spheroid growth conditioned media for self-renewal ability with and without YK-4-250. At the end of 192 h, spheroids were counted for quantitative assessment of the number of spheroids formed. Representative results are shown in FIG. 10. As shown in the figure, YK-4-250 treatment significantly increased the self-renewal ability of YAMC cells compared to vehicle treatment after 4 Gy IR.

Example 7. In Vivo Protective Effects of YK-4-250

Gamma radiation: 7-week-old C57BL/6 mice were exposed to total body irradiation (TBI) 14 Gy gamma ionizing radiation (IR) with air pumped into the chamber during. A Gammacell 40 $^{137}$Cs gamma irradiator was used with a dose rate of 0.8 Gy IR per minute. Dosimetry measurements were performed using Fricke Dosimetry systems. Measured absorbance dose was: Central Dose Rate (0.790 Gy/min±2.9%); 3 o'clock position (0.804 Gy/min±3.8%); and 7 o'clock position (0.808 Gy/min±2.7%). The experiments were performed within 6 months of the dosimetry analysis. All IR treatments were begun in the morning. Animals in the treatment group received three doses of YK-4-250, 10 mg/kg body weight per day, beginning 24 h post-IR. All animals received easy access to liquid gel food and water in the cage.

Crypt survival analysis: Two hours before euthanasia (82 h post-IR), each mouse was intraperitoneally injected with 5-bromo-2'-deoxyuridine (BrdUrd, Sigma Aldrich, St. Louis, Mo.; 200 µL of 5 mg/mL BrdUrd solution in PBS).

Figure 11:
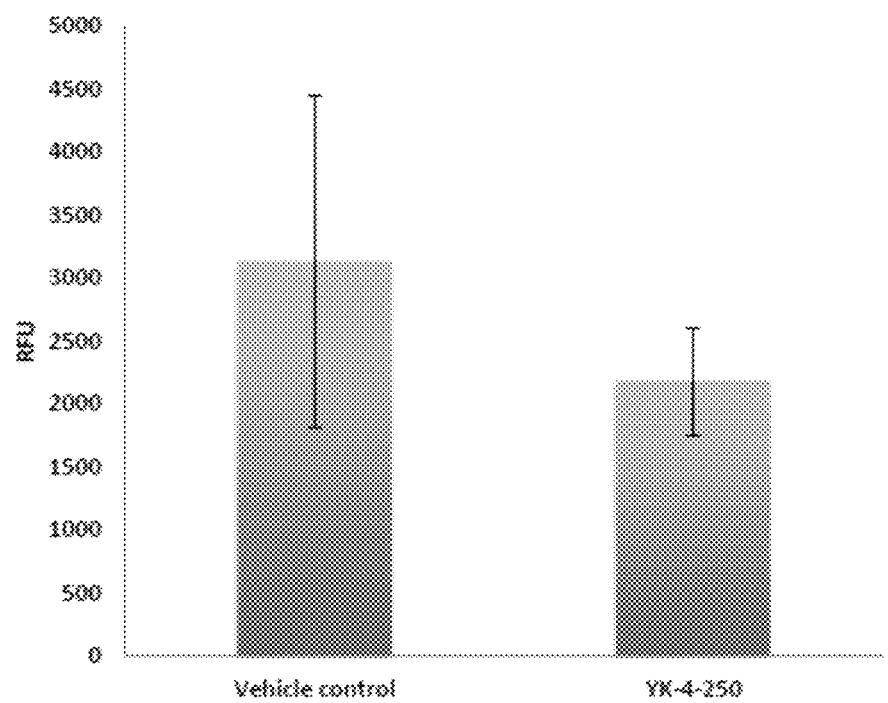
FIG. 11 is a bar graph depicting in vivo whole intestinal epithelial permeability to FITC-dextran 5 days after 14 Gy total body irradiation. Animals received three daily doses of either vehicle control or YK-4-250 beginning 24 h post-IR.

Barrier function study: Two hours before euthanasia (5 d post-IR), each mouse was orally administered (gavage) with 100 µL of FITC-dextran (FITC dextran 4; MW 4000) at a dose of 80 mg/100 g body weight. Serum analysis of FITC concentration was performed in triplicate using Synergy Bio TEK plate reader. Representative results are shown in FIG. 11. As shown in the figure, intestinal epithelial permeability to FITC-dextran was essentially the same for vehicle control and YK-4-250 groups.

Figure 12:
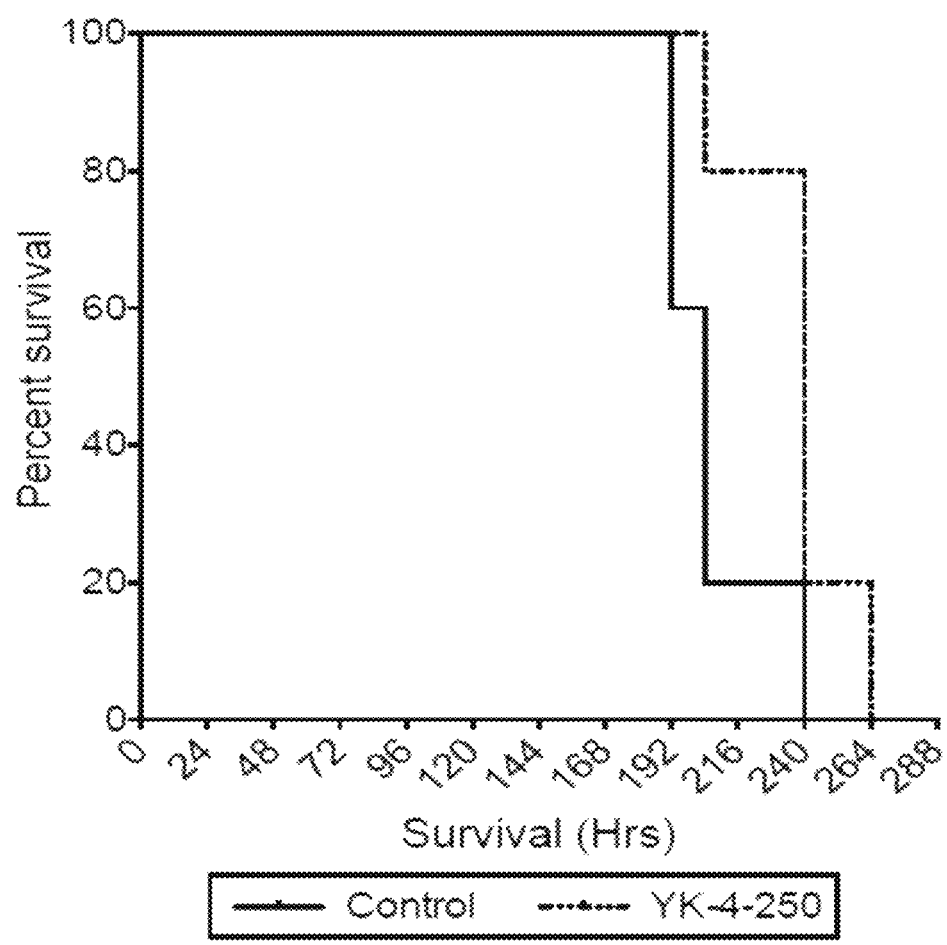
FIG. 12 is a graph depicting survival of mice following 14 Gy total body irradiation. Animals received three daily doses of either vehicle control or YK-4-250 beginning 24 h post-IR.

Overall survival study: Animals following treatment (IR and/or IR+YK-4-250) were allowed to survive. Animals demonstrating bloody stools, lethargy, or unable to move were killed and time of death noted. Survival time of mice in the treatment group was compared with control IR-alone-treated mice. Representative results are shown in FIG. 12. As shown in the figure, median survival for control-treated mice was 204 days, whereas median survival for YK-4-250-treated mice was 240 days. Log-rank (Mantel-Cox) test chi square 3.891; p=0.0486.

INCORPORATION BY REFERENCE

All patents and published patent applications mentioned in the description above are incorporated by reference herein in their entireties.

EQUIVALENTS

Having now fully described several embodiments of the present disclosurein some detail by way of illustration and example for purposes of clarity of understanding, it will be obvious to one of ordinary skill in the art that the same can be performed by modifying or changing the various embodiments within a wide and equivalent range of conditions, formulations and other parameters without affecting the scope of the disclosure or any specific embodiment thereof, and that such modifications or changes are intended to be encompassed within the scope of the appended claims.

The invention claimed is:

1. A method for treating or preventing radiation-induced tissue injury, comprising co-administering to a subject in need thereof a therapeutically effective amount of a compound represented by formula II

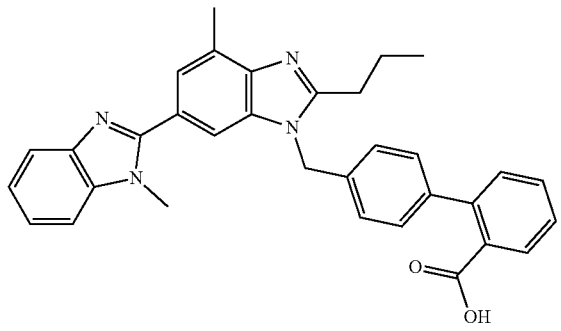

(II)

or a pharmaceutically acceptable salt thereof, and a therapeutically effective amount of a compound represented by formula III

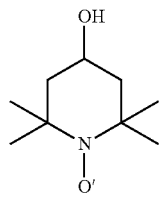

(III)

or a pharmaceutically acceptable salt thereof, thereby treating or preventing radiation-induced tissue injury in the subject.

2. The method of claim 1, wherein the compounds are co-administered prior to exposure of the subject to radiation.

3. The method of claim 1, wherein the compounds are co-administered after exposure of the subject to radiation.

4. The method of claim 1, wherein the radiation-induced tissue injury is acute radiation-induced tissue injury.

5. The method of claim 1, wherein the radiation-induced tissue injury is chronic radiation-induced tissue injury.

6. The method of claim 2, wherein the radiation-induced tissue injury is acute radiation-induced tissue injury.

7. The method of claim 2, wherein the radiation-induced tissue injury is chronic radiation-induced tissue injury.

8. The method of claim 3, wherein the radiation-induced tissue injury is acute radiation-induced tissue injury.

9. The method of claim 3, wherein the radiation-induced tissue injury is chronic radiation-induced tissue injury.

10. The method of claim 1, wherein the tissue comprises gastrointestinal tissue.

11. The method of claim 1, wherein the tissue comprises hematopoietic tissue.

12. The method of claim 1, wherein the tissue comprises neural tissue.

13. The method of claim 1, wherein the compound is administered orally.

14. The method of claim 1, wherein the compound is administered parenterally.

15. The method of claim 1, wherein the subject is a mammal.

16. The method of claim 1, wherein the subject is a human.

17. The method of claim 1, wherein the radiation-induced tissue injury is prevented.

18. The method of claim 1, wherein the radiation-induced tissue injury is treated.

* * * * *